United States Patent [19]

Kantor et al.

[11] Patent Number: 5,149,757
[45] Date of Patent: Sep. 22, 1992

[54] PROCESS TO SYNTHESIZE LIQUID CRYSTALLINE POLYESTERS

[75] Inventors: Simon W. Kantor, Agawam; Robert W. Lenz, Amherst; William J. Ward, Sunderland, all of Mass.

[73] Assignee: University of Massachusetts at Amherst, Amherst, Mass.

[21] Appl. No.: 517,122

[22] Filed: May 1, 1990

[51] Int. Cl.$^5$ .................. C08G 63/00; C08G 67/00; C08G 63/02
[52] U.S. Cl. .................. 528/271; 528/176; 528/272
[58] Field of Search .................. 528/176, 271, 272

[56] References Cited

U.S. PATENT DOCUMENTS 3,772,405 11/1973 Hamb .................. 528/298
3,991,013 11/1976 Pletcher .................. 528/191

Primary Examiner—Harold D. Anderson
Assistant Examiner—T. Mosley
Attorney, Agent, or Firm—Richard P. Fennelly; Louis A. Morris

[57] ABSTRACT

Liquid crystalline polyesters of the aromatic triad type are formed by reaction of an alkylene bis(acetoxybenzoate) monomer and an aromatic dicarboxylic acid monomer with removal of acetic acid by-product therefrom.

6 Claims, 1 Drawing Sheet

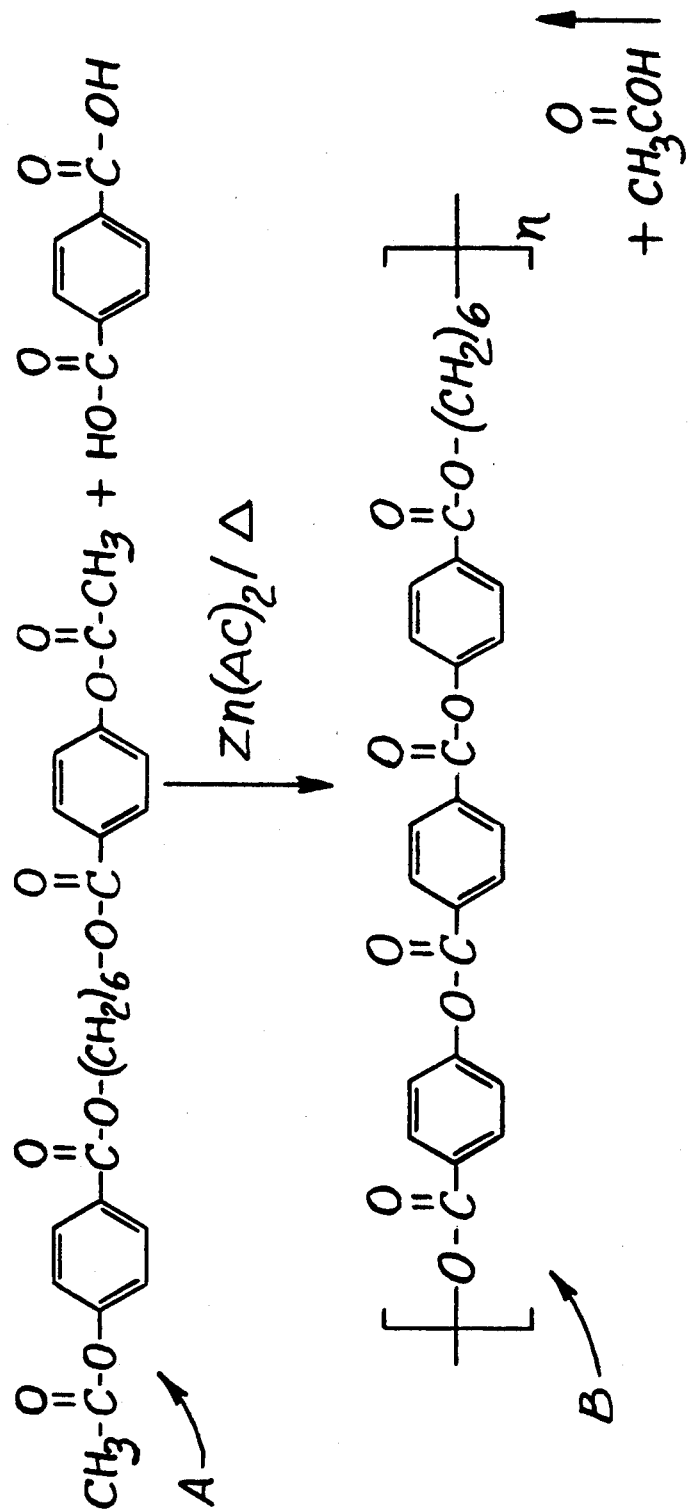

PROCESS TO SYNTHESIZE LIQUID CRYSTALLINE POLYESTERS

BACKGROUND OF THE INVENTION

Liquid crystalline polyesters can be synthesized by step-growth polymerization techniques. Two basic methods are generally used. The first involves growing the polymer from solution involving the reaction of a diol with a diacid chloride. The problem of polymer solubility, however, can be a limiting factor in the preparation of high molecular weight polymers, especially in the case of aromatic polyesters. The second method avoids such problems by carrying out the reaction in the absence of solvent. Such bulk (or melt) polymerization techniques (see V. V. Korshak et al., "Experimental Methods of Bulk Polymerization", Comprehensive Polymer Science, Vol. 5, G. Allen, ed., Pergamon Press, Oxford, 1989), usually involve either the reaction of dicarboxylic acids (or their alkyl esters) with diols or the reaction of diacetates with dicarboxylic acids, in the presence or absence of a catalyst. The bulk method works best when the reacting functionalities are directly attached to the aromatic rings.

It has been shown by previous investigators that the aromatic triad polyester, a preferred embodiment of which is shown by structure (B) in the FIGURE, exhibits a nematic crystalline phase upon melting. A reference which discusses this type of liquid crystalline polyester is C. Ober et al., Polymer J., 14, 9 (1982). Such a polymer has been prepared from solution but had a relatively low molecular weight due to solubility problems.

DESCRIPTION OF THE INVENTION

The instant invention relates to preparation of the aforementioned type of aromatic triad liquid crystalline polymer by reaction of alkylene bis(acetoxybenzoate) monomer with an aromatic dicarboxylic acid monomer to form the desired aromatic triad polyester with liberation of acetic acid by-product.

A representative alkylene bis(acetox-ybenzoate) monomer is depicted by (A) in the FIGURE with the alkylene group being hexamethylene, namely —$(CH_2)_6$—. If desired the phenyl rings can be independently substituted with such substituents as lower alkyl, aryl, halogen, etc. The methylene group can be varied in its length and can be generically depicted as —$(CH_2)_r$— with r ranging from 3 to 8. A further description of certain of these monomers and their process of preparation (e.g., by reaction of an acetoxybenzoic acid with thionyl chloride to form an acetoxybenzoyl chloride which is reacted with a dihydroxy compound HO$(CH_2)_r$OH) is found in "New Monomers for Liquid Crystalline Polyesters", U.S. Ser. No. 517,119, filed May 1, 1990 pending 120.

As depicted in the FIGURE, this monomer (A) can be reacted with a dicarboxylic acid compound, such as terephthalic acid, in the absence of or, preferably in the presence of a catalyst such as zinc acetate, using heat to produce the desired aromatic triad liquid crystalline polyester (B) with acetic acid by-product which is easily removed. The dicarboxylic acid reactant can have its phenyl ring substituted by the same substituents described above. Copolymers with mixtures of monomers, e.g., with 50 mole % of a monomer where r is 4 and 50 mole % of a monomer where r is 6, may be prepared. These ratios can be widely varied to cover the entire compositional range (e.g., 1%–99% to 99%–1%).

The instant process is one which is deemed to allow for synthesis of the type of aromatic triad polyester (B) in increased molecular weight as compared to solution methods. Of considerable importance is that the acidolysis reaction does not occur to any extent between the carboxylic acid function and the internal diol ester groups so that essentially no scrambling of the units occurs. The process produces acetic acid as a by-product which can easily be removed under vacuum (see U.S. Pat. No. 3,772,405 of F. L. Hamb).

The instant invention is further understood by the Examples which follow.

EXAMPLE 1

An amount equalling 3.800 grams of the diacetate monomer, represented by "(A)" in the FIGURE, was combined with 1.427 grams of terephthalic acid and 0.050 gram of zinc acetate, and the solids were thoroughly mixed with a mortar and pestle. The solid mixture was then placed into a reaction tube, and flushed with argon, and a slow stream of argon was passed through the reaction tube. The reaction tube was then placed in a hot salt bath at 180° C., and the temperature was slowly raised to 250° C. over a period of two hours. The reaction temperature was then raised to 270° C. and held there for two and one-half hours. Finally, a high vacuum was applied, and the reaction temperature was raised to 290° C. for one hour. The product was removed and ground, then treated at 215° C. for twenty hours under vacuum to induce further reaction and increase the molecular weight of the product (see German Offen. No. 2,520,820, U.S. Pat. No. 3,991,013, and H. R. Dicke et al., J. Polym. Sci., Polym. Chem. Ed., 21, 2581, 1983). The product was then extracted with methanol and dried in a vacuum oven, to give 2.0 grams of polymer.

The product was examined under an optical polarizing microscope and found to display a nematic schlieren texture. The polymer (B) exhibited a melting point of 241° C., and an isotropization temperature of 345° C., as determined by DSC. The inherent viscosity was measured to be 0.540 dl/g at 45.5° C. in p-chlorophenol.

Analysis for $C_{28}H_{24}O_8$: Calculated: C, 68.84; H, 4.95. Found: C, 68.71; H, 4.79.

EXAMPLE 2

This Example shows the preparation of a triad copolymer (B), where r=4,6 (50/50).

An amount equalling 3.020 grams of the diacetate monomer "(A)", where r=4, was combined with 3.224 grams of the diacetate monomer "(A)", where r=6, and 2.421 grams of terephthalic acid, along with 0.050 gram of zinc acetate. The solids were thoroughly mixed and placed into a reaction tube, and flushed with argon, and a slow stream of argon was passed through the reaction tube. The reaction tube was then placed in a hot salt bath at 180° C.. The reaction temperature was then slowly raised to 295° C. over a period of 6 hours. A high vacuum (less than 0.1 mm Hg) was then applied to the reaction tube with heating at 295° C. for an additional hour. The product was removed and ground, then treated at 180°–192° C. for six hours under vacuum to induce further reaction and increase molecular weight The product was then extracted with methanol and dried in a vacuum oven, to give 2.8 grams of polymer.

The product was examined under an optical polarizing microscope and found to display a nematic schlieren texture. Analysis of the polymer (B), where r=4,6 (50/50), by DSC revealed two endotherm peaks at 174° C. and 204° C. The isotropization temperature was above the decomposition temperature, which began at 308° C. as determined by TGA. The inherent viscosity was 0.42 dl/g at 45.7° C. in p-chlorophenol.

Analysis for $C_{54}H_{44}O_{16}$: Calculated: C, 68.35; H, 4.67. Found: C, 68.10; H, 4.67.

EXAMPLE 3

This Example shows preparation of a triad polymer of the general structure B where the repeating methylene unit is four carbons rather than six.

An amount (4 gm) of diacetate monomer A (with r=4) was combined with 1.603 gm of terephthalic acid and 0.050 gm of zinc acetate and the solids were thoroughly mixed. The solid mixture was then placed into a reaction tube and was flushed with argon and a slow stream of argon was passed through the reaction tube. This reaction tube was then placed in a hot salt bath at 180° C., and the temperature was slowly raised to 285° C. over a period of five hours. A high vacuum (less than 0.1 mm Hg) was applied, and the reaction temperature was raised to 295° C. for one and one-half hours. The product was then removed, was ground and was then treated at 250° C. for two hours under a high vacuum (less than 0.1 mm Hg). The product was then extracted with methanol and was dried in a vacuum oven to give 3.4 gm of polymer.

The product was examined under an optical polorizing microscope and was found to!display a nematic schieren texture. The polymer exhibited a melting point of 243° C.. The isotropization temperature, which was 340° C., as determined by TGA. The inherent viscosity was to be 0.524 dl/g at 45.6° C. in p-chlorophenol.

Analytical calculations for $C_{26}H_{20}O_8$: C, 67.82; H, 4.38. Found: C, 67.40; H,4.32

The foregoing Examples should not be construed in a limiting sense since it is intended to describe only certain embodiments of the instant invention. The scope of protection sought is set forth in the claims which follow.

We claim:

1. A process for forming a liquid crystalline polyester resin of the aromatic triad type which comprises reacting an alkylene bis(acetoxybenzoate) monomer and an aromatic dicarboxylic acid monomer with removal of acetic acid by-product.

2. A process as claimed in claim 1 wherein the alkylene group is $C_3$ to $C_8$ alkylene.

3. A process as claimed in claim 1 wherein a zinc acetate catalyst is additionally present.

4. A process as claimed in claim 1 wherein the aromatic dicarboxylic acid monomer is terephthalic acid.

5. A process as claimed in claim 4 wherein the alkylene group is $C_3$ to $C_8$ alkylene.

6. A process as claimed in claim 5 wherein a zinc acetate catalyst is additionally present.

* * * * *